(12) United States Patent
Fontaine et al.

(10) Patent No.: US 6,447,540 B1
(45) Date of Patent: *Sep. 10, 2002

(54) STENT DEPLOYMENT DEVICE INCLUDING SPLITTABLE SLEEVE CONTAINING THE STENT

(75) Inventors: Arthur B. Fontaine; Susan DosPassos, both of Bellevue, WA (US); Brian L. Bates, Bloomington, IN (US); Scott E. Boatman, Bloomington, IN (US); Michael C. Hoffa, Bloomington, IN (US); Thomas A. Osborne, Bloomington, IN (US)

(73) Assignee: Cook Incorporated, Bloomington, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/971,113

(22) Filed: Nov. 14, 1997

Related U.S. Application Data (60) Provisional application No. 60/030,937, filed on Nov. 15, 1996.

(51) Int. Cl.[7] .................................................. A61F 2/06
(52) U.S. Cl. ....................................... 623/1.12; 606/108
(58) Field of Search ................................ 606/108, 192, 606/194, 193–198; 604/8, 96; 623/1, 2, 11, 12

(56) References Cited

U.S. PATENT DOCUMENTS

| 3,677,243 A | 7/1972 | Nerz |
| 3,877,429 A | 4/1975 | Rasumoff |
| 4,105,732 A | 8/1978 | Slingluff |
| 4,166,469 A | 9/1979 | Littleford |
| 4,182,582 A | 1/1980 | Youval et al. |
| 4,306,562 A | 12/1981 | Osborne |

(List continued on next page.)

FOREIGN PATENT DOCUMENTS

| EP | 0732087 | 9/1996 |
| WO | 9317636 | 9/1993 |
| WO | 9511055 | 4/1995 |

Primary Examiner—Michael H. Thaler
(74) Attorney, Agent, or Firm—Richard J. Godlewski (57) ABSTRACT

A stent deployment device (10) includes a catheter (12), a stent (14) positioned on the catheter (12), and a sleeve (16) carried on the catheter (12). The sleeve (16) has a portion (18) extending fully over and containing the stent (14). The stent deployment device (10) also includes a mechanism (20) for splitting at least the portion (18) of the sleeve (16) extending over the stent (14) and, preferably, for splitting the entire sleeve (16). Splitting of the sleeve portion (18) permits expansion of the stent (14). The mechanism (20) can include an inflatable, nondistending balloon (22) carried on the catheter (12), the stent (14) and the sleeve portion (18) being positioned over the balloon (22). The stent (14) can be self-expanding or can be expanded by the balloon (22) itself. Alternatively, the mechanism (20) can include a bulbous end (24) on the catheter (12). Longitudinal movement of the bulbous catheter end (24) with respect to the sleeve (16) splits at least the sleeve portion (18), permitting expansion of the stent (14). As further alternatives, the mechanism (20) can include a garrote (66) connected to the sleeve or a partial segment (62) of the sleeve (16) folded back alongside the stent (14). The sleeve (16) can be the same length as the catheter (12) or can be shorter than the catheter (12). In the former case, the mechanism (20) can include a pair of graspable wings (56) for splitting the full length of the sleeve (16). It is preferred that at least the portion (18) of the sleeve (16) extending over the stent (14) includes a longitudinally extending structure 46 for ensuring that the sleeve portion (18) will in fact split upon operation of the mechanism (20).

18 Claims, 8 Drawing Sheets

U.S. PATENT DOCUMENTS

| | | |
|---|---|---|
| 4,402,685 A | 9/1983 | Bühler et al. |
| 4,412,832 A | 11/1983 | Kling et al. |
| 4,581,019 A | 4/1986 | Curelaru et al. |
| 4,581,025 A | 4/1986 | Timmermans |
| 4,596,559 A | 6/1986 | Fleischhacker |
| 4,601,713 A * | 7/1986 | Fuqua ........................ 604/280 |
| 4,710,181 A * | 12/1987 | Fuqua ........................ 604/280 |
| 4,747,833 A | 5/1988 | Kousai et al. |
| 4,776,846 A | 10/1988 | Wells |
| 4,781,690 A | 11/1988 | Ishida et al. |
| 4,828,550 A | 5/1989 | Kurimoto |
| 4,830,805 A | 5/1989 | Kousai et al. |
| 4,865,593 A | 9/1989 | Ogawa et al. |
| 4,883,468 A | 11/1989 | Kousai et al. |
| 4,887,997 A | 12/1989 | Okada |
| 4,952,359 A | 8/1990 | Wells |
| 4,983,168 A | 1/1991 | Moorehead |
| 5,015,231 A * | 5/1991 | Keith et al. .................... 604/96 |
| 5,188,605 A | 2/1993 | Sleep |
| 5,304,119 A | 4/1994 | Balaban et al. |
| 5,316,543 A | 5/1994 | Eberbach |
| 5,324,261 A * | 6/1994 | Amundson et al. ........... 604/96 |
| 5,464,419 A | 11/1995 | Glastra |
| 5,571,169 A | 11/1996 | Plaia et al. |
| 5,647,857 A * | 7/1997 | Anderson et al. ........... 604/264 |
| 5,700,286 A * | 12/1997 | Tartaglia et al. ................ 623/1 |
| 5,766,203 A * | 6/1998 | Imran et al. ................... 604/96 |

\* cited by examiner

STENT DEPLOYMENT DEVICE INCLUDING SPLITTABLE SLEEVE CONTAINING THE STENT

CROSS-REFERENCE TO RELATED APPLICATIONS

This application claims priority of provisional application Serial No. 60/030,937 filed Nov. 15, 1996.

TECHNICAL FIELD

This invention relates generally to medical devices and procedures for using such devices and, more particularly, to devices which are introduced into a vessel, cavity, or duct in a human or veterinary patient.

BACKGROUND OF THE INVENTION

Catheters have long been used in a wide variety of medical procedures for establishing, reestablishing or maintaining passages, cavities, or lumens in vessels, organs or ducts in human and veterinary patients. Such vessels and the like include those of the vascular system, the biliary tract (including the common bile and other ducts) and the urinary tract (including the kidney, the bladder, the ureters and the urethra), as well as the esophagus, the trachea, the intestines, the colon, the rectum, the sinus tract, the fallopian tubes, the cervix and the vagina, among others. All of these may be subject to stricture or narrowing which requires dilation. For example, blood vessels can be blocked or narrowed by arteriosclerosis (atherosclerosis), while esophageal strictures can arise from individual anatomical differences, or from diseases such as connective tissue disorder or cancer.

Catheters useful for dilating or enlarging regions in such vessels and the like often include a nondistending, inflatable balloon which can be positioned across a particular stricture or narrowed region. For example, in percutaneous transluminal angioplasty (PTA), a catheter bearing a collapsed balloon is introduced into a patient's blood vessel and advanced until the balloon lies across a site to be dilated. The balloon of the catheter is then inflated with a fluid so as to widen the vessel or the like, without trauma to the vessel at the site of treatment.

It is sometimes necessary or desirable to provide the site of dilation with a device or structure which prevents subsequent stenosis (closure) of the site. Stents are a known class of surgical devices which are useful for maintaining open lumens. For example, U.S. Pat. No. 4,580,568 (C. Gianturco, Apr. 8, 1986), U.S. Pat. No. 4,739,762 (J.C. Palmaz, Apr. 26, 1988) and U.S. Pat. No. 4,907,336 (C. Gianturco, Mar. 13, 1990) all disclose stents having a cylindrical shape. Each of these stents is contained by a removable sheath so as to facilitate its introduction into a blood vessel or other body portion. (Stents embodying the invention disclosed in the first of these patents is sold under the name "Z-stent," a trade name of Cook Incorporated.) In the use of each, the sheath is withdrawn after the stent is positioned at the desired site, and only after withdrawal of the sheath is the stent expanded by a balloon catheter ('762 and '336), or is the stent permitted to self-expand ('568). The expanded stent prevents subsequent stenosis of the site.

In the use of these and other stents, it is highly desirable to minimize the cross-sectional area (profile) of the collapsed stent, as well as that of the retractable sheath and of the catheter on which they are carried. Accordingly, the sheath must typically be made of a thin-walled material which contains the stent in close proximity to the balloon. The combination of these requirements often makes it difficult to retract such a sheath without stretching the sheath or displacing the stent on the balloon. Such a sheath can stretch so much as to fail to uncover the stent, rendering the system for deploying the stent useless. Furthermore, such a sheath can also displace the stent and prevent proper deployment. Moreover, the delivery of a stent to the site of dilation on the same balloon which dilates the site can be subject to other drawbacks. Most notably, friction between the containment sheath and the catheter or stent can make it very difficult to slide the sheath far enough to expose the stent for proper expansion. This drawback can be particularly acute with catheters and stents of small diameter.

U.S. Pat. No. 5,464,419 (H. Glastra, Nov. 7, 1995) discloses a PTA device which appears to lack any sheath at all for containing a stent. Rather, the device includes a spirally wound stent of specific construction which is held in an unexpanded configuration by biologically degradable, thin cords 12. The cords 12 break during expansion of the stent, caused by inflation of a PTA balloon positioned within the spiral stent. The disclosed device can be subject to several drawbacks during use, however. The thin cords 12 are spaced apart, so that the balloon and stent would presumably experience uneven initial expansion in the spaces between the cords. Indeed, the spaced cords pose the potential risk of cutting, breaching or damaging the stent during expansion. Prior to deployment, the spaced cords can give the stent and balloon an irregular degree of stiffness along their length, making the device somewhat more likely to kink during the PTA procedure. Further, the cords can be difficult to affix to the stent, especially to stents of relatively small diameter, such as those intended for deployment in the vascular system.

U.S. Pat. No. 5,316,543 (M. A. Eberbach, May 31, 1994) discloses an apparatus useful in the laparoscopic treatment of hiatal hernias, which includes a rigid outer sleeve having longitudinal recesses and flanges for manual splitting of the sleeve. The patent appears to contain no disclosure or suggestion of the use of such a sleeve for containing a stent prior to deployment of the stent, nor any disclosure or suggestion of any way in which the sleeve could be modified to be used in conjunction with a stent. Moreover, the sleeve is disclosed as being rigid, while the sheaths employed for deploying stents (particularly stents to be positioned in the vascular system) must usually have good flexibility.

It would be highly desirable to have a device or method for deploying a stent which did not require retraction or withdrawal of a containment sheath prior to expansion of the stent. It would also be highly desirable to discover such a device or method which was relatively low cost, which was of relatively straight-forward construction, which possessed high reliability during use, which was easy to remove from the patient if complications arose prior to expansion of the stent, and which did not possess discrete threads which might otherwise damage the stent or catheter during use, or interfere with positioning of the stent.

SUMMARY OF THE INVENTION

The foregoing problems are solved and a technical advance is achieved in an illustrative stent deployment device having a catheter and a stent positioned on the catheter. Applicant has discovered that a splittable sleeve which is carried on the catheter, and which includes a portion extending over, more preferably fully over, and containing the stent, can successfully maintain the stent in a collapsed condition during its deployment at a desired location within a vessel or the like by the catheter, without requiring prior withdrawal or retraction of the sleeve. More particularly, Applicants have discovered that expansion of the collapsed stent can be performed by actuation of a mechanism for splitting at least the portion of the sleeve extending over the stent.

In regard to the present invention, "stent" is intended to have a broad meaning, and to include not only conventional stents, but also implants, prostheses and other devices which can be positioned within a human or veterinary patient by a catheter. "Sleeve" similarly is intended to have a broad meaning, and to include sheaths, tubes and catheters, as well as sleeves. "Split" is intended to include any way in which the sleeve is severed so as to permit expansion of the stent and removal of the sleeve from the patient, and therefore encompasses splitting, tearing, ripping, fracturing, breaking, bursting, separating and fissuring of the sleeve. Lastly, "fully" is intended to mean merely that the portion of the sleeve extending over the stent completely encircles the stent and covers at least a substantial portion of the stent (preferably, at least the majority of the stent) in a longitudinal direction.

Splitting of the portion of the sleeve over the stent advantageously obviates the frictional resistance to withdrawal of the sleeve that would otherwise result from containment of the sleeve portion upon the stent. The substantial coverage of the sleeve by the stent portion provides the device of the present invention with good uniformity of resistance to kinking during use. The stent can be deployed rapidly with the device of the present invention because no time is wasted in attempting to remove the sleeve from the patient before expansion of the stent occurs. Any balloon employed in the present invention is advantageously subjected to relatively uniform force during expansion, obviating any risk of damage to the balloon or stent during expansion. Also, the device is relatively easy to remove in case unexpected complications require interruption of the deployment procedure.

In a first aspect, the present invention is directed to a stent deployment device first comprising a catheter, a stent positioned on the catheter, and a sleeve carried on the catheter, the sleeve having a portion extending fully over and containing the stent. The stent deployment device of the present invention further comprises a mechanism for splitting at least the portion of the sleeve extending over the stent, thereby permitting expansion of the stent. In a preferred embodiment of this aspect, the sleeve-splitting mechanism comprises an inflatable balloon carried on the catheter, and the stent and the portion of the sleeve extending over the stent are positioned over the balloon. Inflation of the balloon splits at least the portion of the sleeve and permits expansion of the stent. The stent can be self-expanding, or can be expanded by the expansion experienced by the balloon itself during inflation.

The sleeve can be shorter in length than the catheter or can be substantially the same length as the catheter. In either case, the sleeve can include an end fixed to the catheter, or the sleeve can be recessed in the catheter, to prevent longitudinal movement of the sleeve along the catheter. Alternatively, the sleeve can be slidable with respect to the catheter after the portion of the sleeve over the stent has been split.

The sleeve is preferably indistensable and can be composed of a medical grade material such as nylon, polytetrafluoroethylene, polyethylene or a polycaprolactam. A lubricious surface can be provided on the sleeve.

The lubricious surface can comprise a layer of a hydrophilic material on the sleeve or can be formed by surface modification of the sleeve.

Without regard to the length of the sleeve itself, the portion of the sleeve over the stent can be severable from the remainder of the sleeve. In such a case, the portion of the sleeve over the stent remains in the vessel after deployment of the stent. It is preferred, but not required, that at least this severed portion of the sleeve is composed of a medical grade, biodegradable material.

Preferably, at least the portion of the sleeve extending over the stent includes a preferentially splittable, longitudinally extending structure. This structure ensures that the sleeve portion will in fact split upon actuation of the splitting mechanism. The preferentially splittable structure can comprise at least one area of reduced radial thickness. Alternatively, the preferentially splittable structure can comprise splittable nylon such as, for example, a plurality of co-extruded nylon strips.

In another preferred embodiment of this first aspect of the present invention, the sleeve includes a proximal end opposite the portion extending over the stent, and the splitting mechanism comprises a means for splitting the entire length of the sleeve between the proximal sleeve end and the portion of the sleeve extending over the stent. The splitting means can comprise a pair of graspable wings on the proximal end of the sleeve. Alternatively, the splitting means can comprise a partial sleeve segment folded back alongside and extending proximally of the stent, whereby withdrawal of the partial sleeve segment splits the sleeve.

In still another preferred embodiment of this first aspect of the present invention, the splitting mechanism comprises a garrote having a proximal end and a distal end, the distal end of the garrote being connected to the sleeve, and the garrote extending between the stent and the sleeve. Withdrawal of the proximal end of the garrote splits at least the portion of the sleeve over the stent, permitting expansion of the stent.

In yet another preferred embodiment of this first aspect of the present invention, the splitting mechanism comprises a string that passes through the sleeve and out the distal end thereof. The string is looped back on the exterior of the sleeve and through a side port or access hole in the vicinity of the proximal end of the stent and into the passage of the sleeve and out the proximal end thereof. Either end of the string is then pulled to split the sleeve or at least that portion over the stent, thereby permitting expansion of the sleeve.

In still yet another preferred embodiment of this first aspect of the present invention, the splitting mechanism comprises a bulbous end on the catheter. Longitudinal movement of the bulbous catheter end with respect to the sleeve splits at least the portion of the sleeve extending over the stent, thereby permitting expansion of the stent. The bulbous end on the catheter can be solid or can be an inflatable balloon.

In a second aspect, the present invention is directed to a device comprising a specific combination of the preferred elements described above. More particularly, the second aspect of the present invention is directed to such a device as broadly described, but in which at least the portion of the sleeve extending over the stent includes the preferentially splittable, longitudinally extending structure as described; in which the mechanism for splitting at least the sleeve portion comprises an inflatable balloon carried on the catheter; in which the stent and the portion of the sleeve extending over the stent are positioned over the balloon; and in which expansion of the balloon during inflation (a) splits at least the portion of the sleeve, and (b) expands the stent.

In a final aspect, the present invention is directed to a device comprising a further combination of specific preferred elements described above. More particularly, the final aspect of the present invention is directed to a device as described with regard to the second aspect of the invention, but in which the sleeve is substantially the same length as the catheter and has a proximal end fixed to the catheter; in which the sleeve is composed of nylon; and in which the preferentially splittable, longitudinally extending structure included in at least the portion of the sleeve extending over the stent comprises at least one area of reduced radial thickness.

Again, the present invention provides a stent deployment device which is highly advantageous over prior devices and methods of stent deployment. Splitting of the sleeve portion over the stent obviates the frictional resistance to withdrawal of the sleeve that would otherwise result from containment of the sleeve upon the stent. The device possesses good uniformity of resistance to kinking during use. The device of the present invention is often capable of deploying a stent rapidly, because no time is wasted in attempting to remove the sleeve from the patient before expansion of the stent occurs The device can be manufactured in a straight-forward manner and at relatively low cost. If a balloon is employed on the catheter, the balloon is advantageously subjected to relatively uniform force during expansion, obviating any risk of damage to the balloon or stent during expansion. Also, since the device is inserted as a single unit, it is relatively easy to remove in case unexpected patient complications require interruption of the deployment procedure.

BRIEF DESCRIPTION OF THE DRAWING

A better understanding of the present invention will now be had upon reference to the following detailed description, when read in conjunction with the accompanying drawing, wherein like reference characters refer to like parts throughout the several views, and in which.

DETAILED DESCRIPTION

Figure 1:
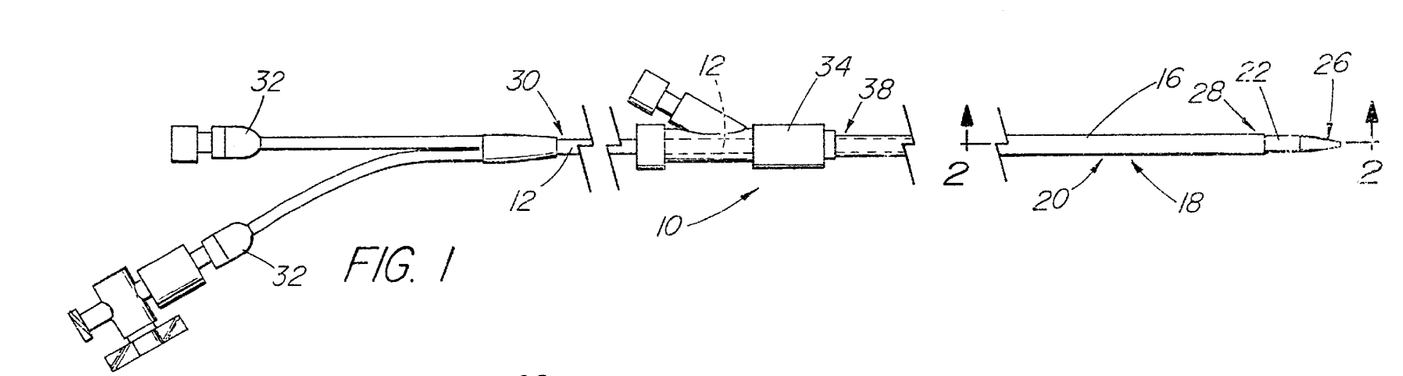
FIG. 1 is a side view of a first preferred embodiment of a stent deployment device of the present invention.
Figure 2:
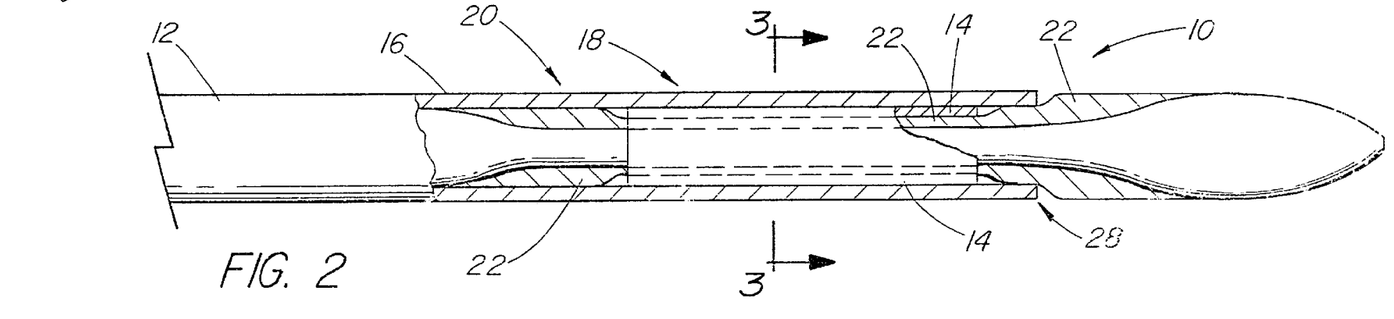
FIG. 2 is an enlarged sectional view of the deployment device of FIG. 1 taken along line 2—2.
Figures 3, 4, 5:
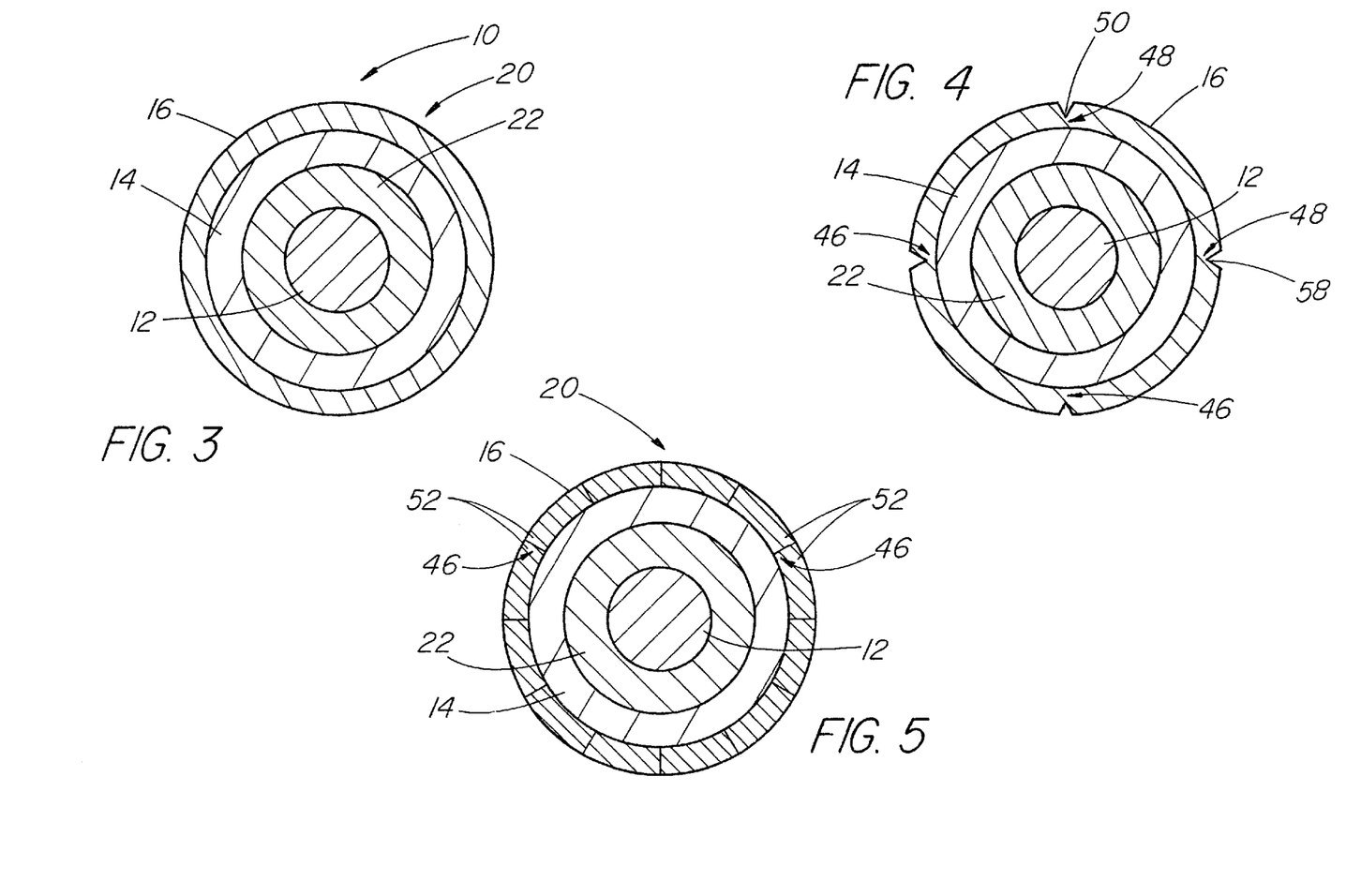
FIG. 3 is an enlarged cross-sectional view of the deployment device of FIG. 2 taken along line 3—3.
FIGS. 4 and 5 are cross-sectional views of further preferred embodiments of a stent deployment device of the present invention, similar to the view shown in FIG. 3.

With reference first to FIGS. 1 through 3, a first preferred embodiment of the stent deployment device 10 of the present invention is there shown, comprising a catheter 12, a stent 14 positioned on the catheter 12, and a sleeve 16 carried on the catheter 12. The sleeve 16 has a portion 18 extending fully over and containing the stent 14. The stent deployment device 10 further comprises a mechanism 20 for splitting at least the portion 18 of the sleeve 16 extending over the stent 14. Actuation of the mechanism 20 splits at least the portion 18 and permits expansion of the stent 14.

The stent 14 can be self-expanding upon splitting of the sleeve portion 18, or can be expanded by the splitting mechanism 20 itself. In either case, in this first embodiment of the present invention, the splitting mechanism 20 comprises an inflatable, nondistending balloon 22 carried on the catheter 12 near the distal tip 26 of the catheter 12. The stent 14 and the portion 18 of the sleeve 16 extending over the stent 14 are thus positioned over the balloon 22, with the distal end 28 of the sleeve 16 lying just distally of the stent 14.

One or more conventional fluid couplings 32 are provided at the proximal end 30 of the catheter 12, through which a pressurized fluid is supplied to the balloon 22 through a lumen for inflation. Inflation of the balloon with the fluids need only proceed for the balloon to extend radially outwardly to expand the sleeve until it splits at least the portion 18 of the sleeve 16 extending over the stent 14, permitting expansion and deployment of the stent 14. Preferably, in this embodiment the stent 14 is expanded by expansion of the balloon 22 during its inflation by the fluid. Although not depicted, another lumen extends longitudinally through the catheter between the distal end thereof and one of the proximal couplings 32. This lumen is typically utilized for passing the catheter over a wire guide that has already been positioned in a vessel.

As indicated, the stent 14 can be any type of implant, prosthesis or stent deliverable by catheter. Without limiting the scope of the invention, and only by way of example, in vascular applications the stent 14 can conveniently comprise the balloon-deliverable Palmaz or Gianturco stents described above. The stent 14, of course, must survive any containment or compression by the sleeve portion 18 before the portion 18 is split, and must survive any compression experienced during splitting of the sleeve portion 18.

Figures 6, 7:
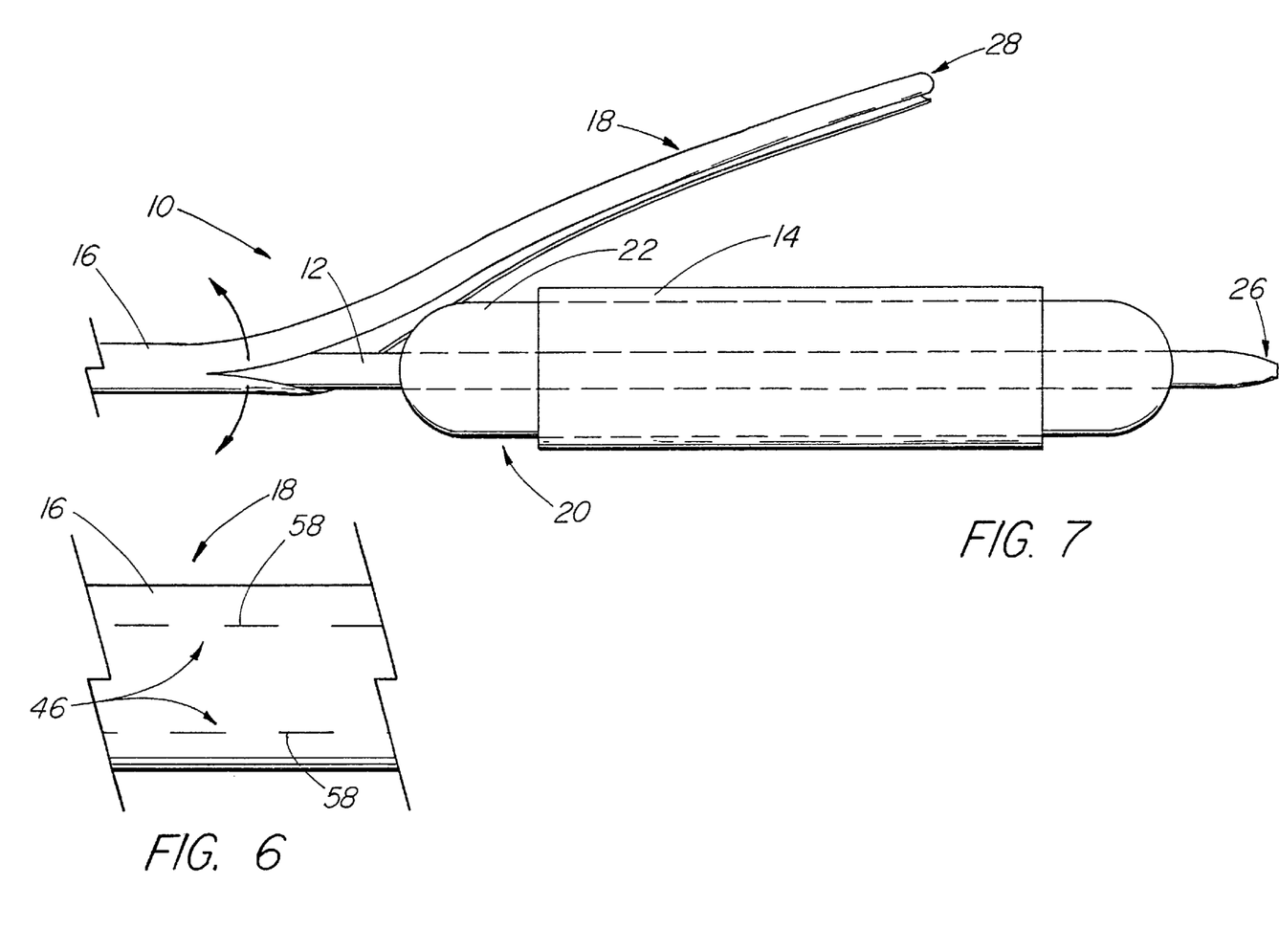
FIG. 6 is an enlarged side view of a portion of another preferred embodiment of the stent deployment device of the present invention.
FIG. 7 is a side view of an enlarged portion of the preferred embodiment of the deployment device of FIG. 1 during use.

Regardless of the specific construction of the stent 14 employed, the resulting expansion and deployment of the stent 14 is generally shown in FIG. 7.

Figure 8:
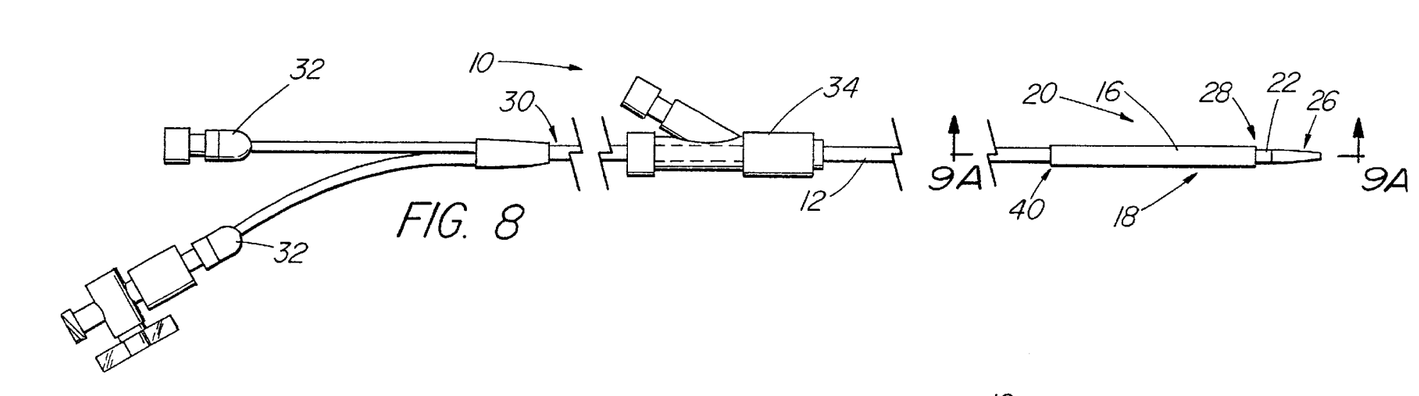
FIG. 8 is a side view of another preferred embodiment of the present invention, similar to the view shown in FIG. 1.
Figure 9A:
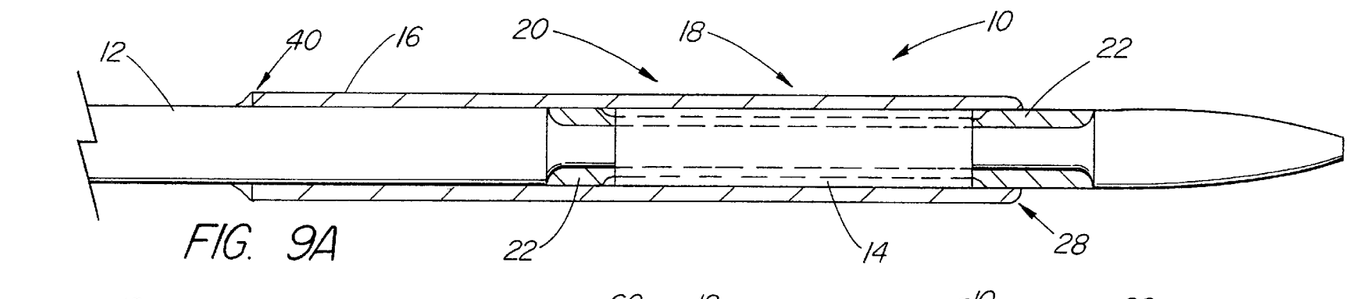
FIG. 9A is a partial cross-sectional view of the deployment device of FIG. 8 taken along line 9A—9A.

In the first preferred embodiment of the device 10, the sleeve 16 is substantially the same length as the catheter 12 and includes a proximal end 38 fixed to the catheter 12, for example, fixed near the proximal end 30 of the catheter 12 at the coupling 34. Alternatively, as shown in FIGS. 8 and 9A, the sleeve 16 can be much shorter in length than the catheter 12, and can include a proximal end 40 fixed to the catheter 12 close to the stent 14.

The sleeve 16 can be composed of any of a variety of materials, some more suited to particular applications than others. Sound medical judgment should be employed in selecting the material for the sleeve 16.

The sleeve 16 should of course be composed of an indistensable material, so that the sleeve portion 18 is sure to split upon actuation of the mechanism 20. The sleeve 16 should also be composed of a medical grade material, which can be either physiologically inert or biodegradable.

Suitable inert materials for the sleeve 16 include nylon, polyethylene, a polycaprolactam or polytetrafluoroethylene (PTFE). Nylon is preferred, especially in comparison to PTFE, since the latter can be subject to recoil after being drawn over the stent 14. If PTFE is employed, it may be advantageous to use scribed or molecular oriented PTFE, so as to facilitate splitting of the sleeve 16 or sleeve portion 18.

Figures 10, 11A, 11B, 12:
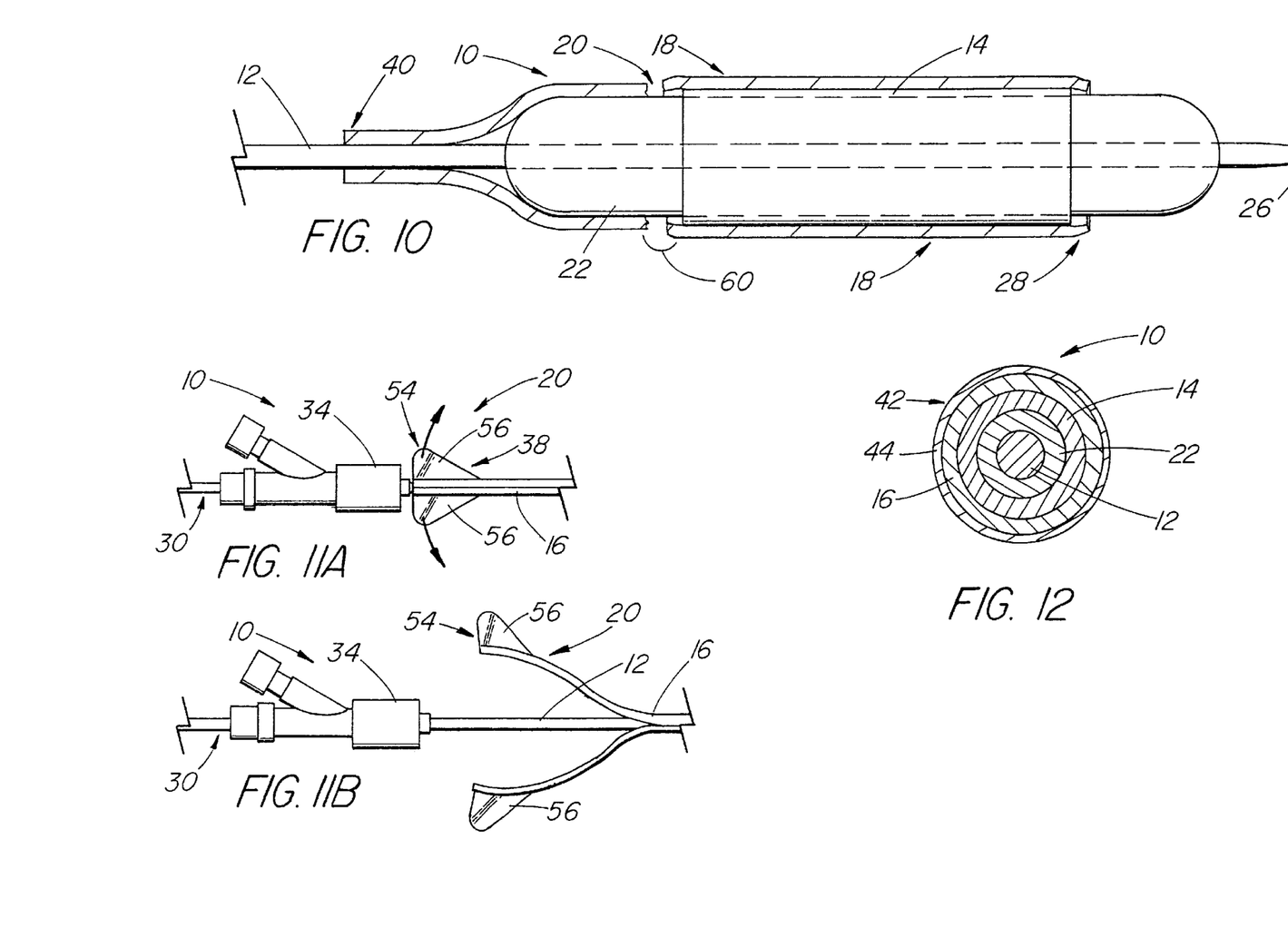
FIG. 10 is a partial cross-sectional view of the deployment device of FIG. 9B during use.
FIG. 11A is a side view of a portion of yet another preferred embodiment of the deployment device of the present invention.
FIG. 11B is a side view of the deployment device of the present invention of FIG. 11A during use.
FIG. 12 is a cross-sectional view of a further preferred embodiment of the present invention, similar to the views shown in FIGS. 3 through 5.

As shown in FIG. 12, a lubricious surface 42 can be provided on the sleeve 16 to facilitate advancement of the device 10 through the vessel or the like into which the stent 14 is introduced. The lubricious surface 42 can be formed by surface modification of the sleeve 16, for example, by ion beam bombardment or implantation, which is commercially available from Spire Corporation, Bedford, Mass. Alternatively, the lubricious surface 42 can comprise a separate layer 44 of a hydrophilic material placed on the sleeve 16.

When the sleeve 16 is composed of an inert material, splitting of the sleeve portion 18 or of the whole sleeve 16 can be facilitated by the inclusion of a preferentially splittable, longitudinally extending structure 46 in at least the sleeve portion 18. The preferentially splittable structure 46 ensures that there will be at least one location at which the sleeve portion 18 readily splits. As shown in FIG. 4, the preferentially splittable structure 46 can comprise at least one area 48, preferably several areas 48, of reduced radial thickness. Such areas 48 can be formed by grooves, inword V-shaped notches, scores, nicks or the like. Alternatively, as shown in FIG. 5, the preferentially splittable structure 46 can comprise splittable nylon such as, for example, a plurality of coextruded nylon strips 52 or plurality of adjacent strips of different material, which forms a tubular structure. This tubular structure forms the sleeve portion 18. As a result, the sleeve portion 18 will split between adjacent strips 52 upon actuation of the splitting mechanism 20. As yet another alternative, as shown in FIG. 6 the preferentially splittable structure 46 can be formed as a spaced plurality of circumferentially offset perforations, such as slits 58, cut into at least the sleeve portion 18.

Figure 9B:
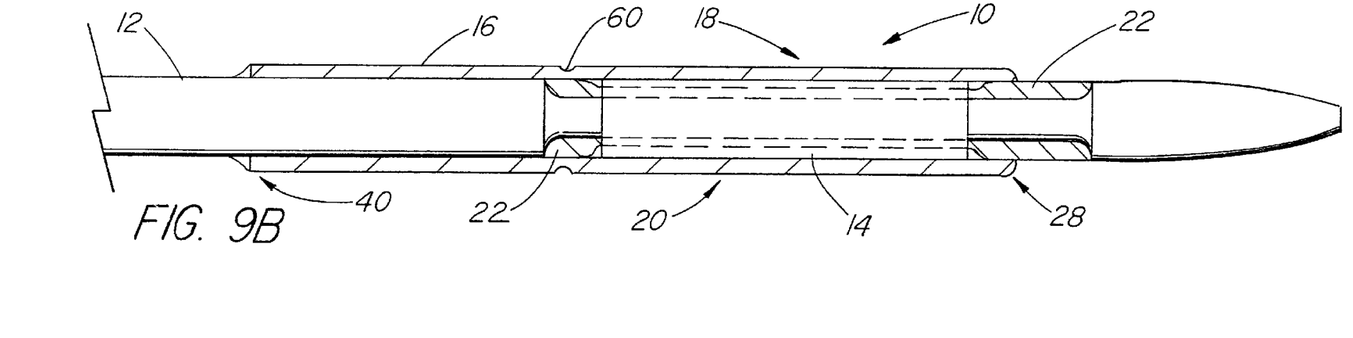
FIG. 9B is a partial cross-sectional view of another preferred embodiment of the deployment device of the present invention, similar to the view shown in FIG. 9A.

When either the sleeve portion 18 or the entire sleeve 16 is composed of a biodegradable material, it is possible to allow part or all of the sleeve portion 18 to become severed from the remainder of the sleeve 16 and remain between the stent 14 and the wall of the vessel or the like in which the stent 14 is deployed. As shown in FIG. 9B, the sleeve 16 can include a circumferential groove 60 allowing such severing upon actuation of the splitting mechanism, that is, upon inflation of the balloon 22. The result is shown in FIG. 10.

A variety of biodegradable materials are expected to be useful for the sleeve 16 or sleeve portion 18. Such materials include polyethylene, polypropylene and polyoxypropylene glycolic sugars, as well as polylactic sugars. The polylactic sugars are expected to degrade much more slowly than the glycolic sugars. The selection of a suitable material for a particular stent and application should be well within the sound medical judgment of those skilled in this area.

Again, it is not necessary, but merely preferred, that any sleeve portion 18 left in the patient be biodegradable. The inert materials disclosed above are also suited to remain in the patient between the deployed stent 14 and the wall of the vessel or other site where the stent 14 is deployed.

In the embodiments disclosed above, the sleeve 16 has been described as being fixed to the catheter 12. In alternative preferred embodiments, however, the sleeve 16 need not be fixed to the catheter 12, but rather can be slidable with respect to the catheter 12 after the sleeve portion 18 has been split by the splitting mechanism 20. Indeed, such sliding can make the sleeve 16 capable of being split along its entire length. In the following embodiments, this lack of affixment permits the catheter 12 to be other than a balloon-type catheter. Self-expanding stents 14 are preferred for use in the following embodiments.

More particularly, as shown in FIGS. 11A and 11B, the splitting mechanism 20 can comprise a means 54 for splitting the entire sleeve 16 between its proximal end 38 (at the end opposite the sleeve portion 18 and remote there from) and the sleeve portion 18. Preferably, the splitting means 54 comprises a pair of graspable wings 56 at the proximal end 38 of the sleeve 16. "Wings" is a broad term, intended to be generic to a wide variety of graspable elements such as grips, flaps, tabs, ears and the like. Movement of the wings 56 in end opposite directions (the unlabeled arrows in FIG. 11A) splits the sleeve 16 along its entire length, including the portion 18 extending over the stent 14, thereby withdrawing the pieces of the sleeve 16 from the patient and allowing deployment of the stent 14.

Figures 13A, 13B, 13C:
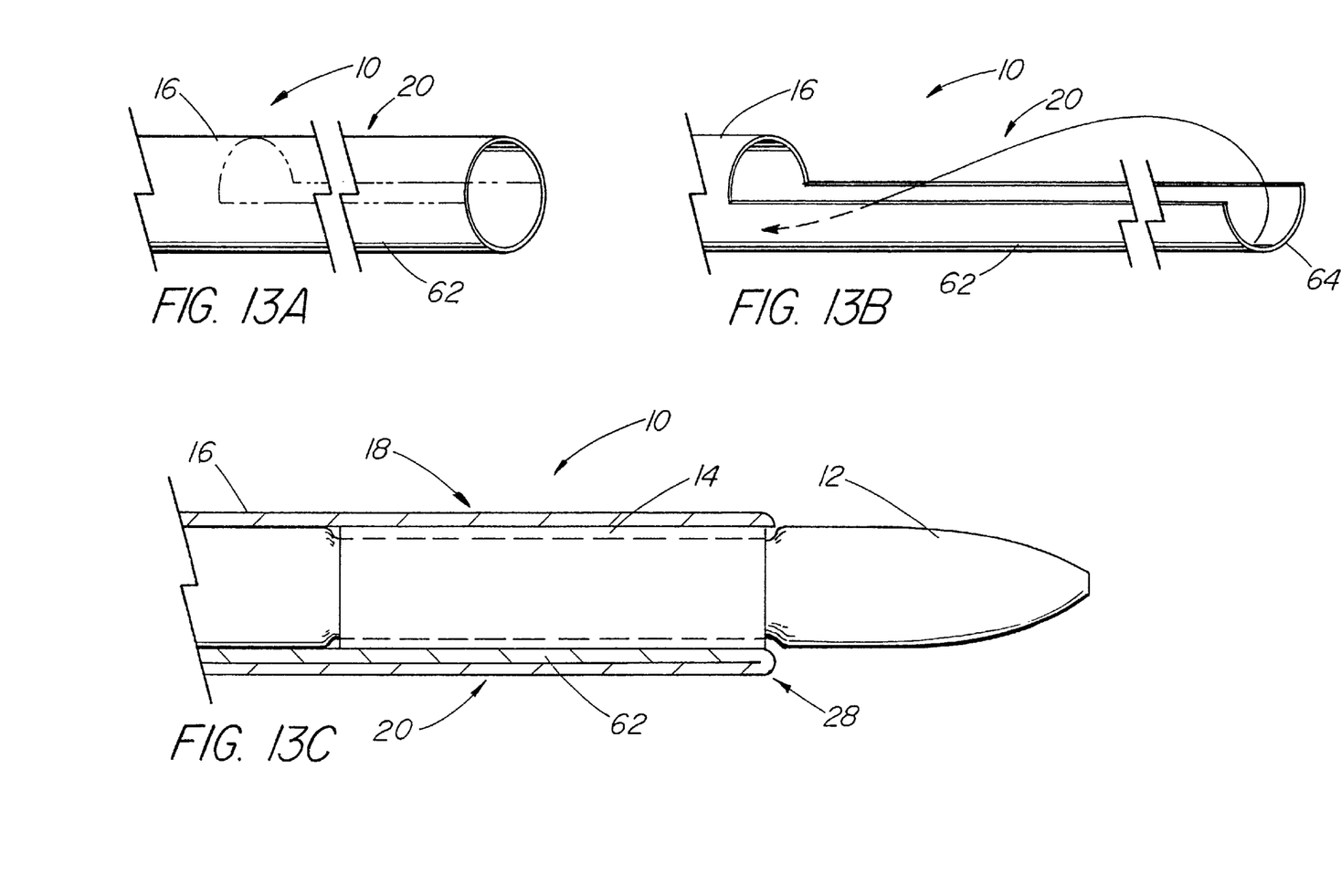
FIGS. 13A and 13B are perspective views showing preliminary steps in constructing another preferred embodiment of the present invention.
FIG. 13C is a cross-sectional view of a portion of the preferred embodiment of the present invention resulting from the steps shown in FIGS. 13A and 13B.

Alternatively, as shown in FIGS. 13A, 13B and 13C, the splitting means 54 can comprise a partial sleeve segment 62 folded back alongside and extending proximally of the stent 14. The sleeve segment 62 includes a graspable, proximal end 64, allowing the sleeve segment 62 to be withdrawn, thereby splitting the sleeve 16. Scribed or molecular oriented PTFE is the preferred material for the sleeve 16 in this embodiment.

In either of these embodiments of the device 10, it is desirable to position the previously described lubricious surface 42 on the inside of the sleeve 16, rather than on the outside of the sleeve 16, so as to reduce friction between the sleeve 16 and the catheter 12.

Figure 14:
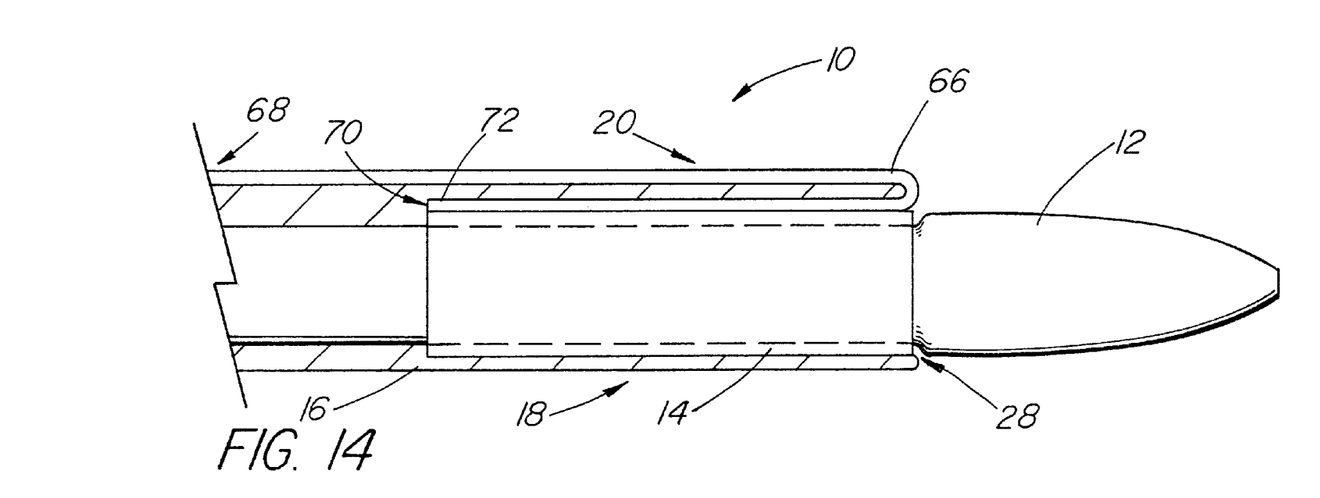
FIG. 14 is a cross-sectional view of a portion of a still further preferred embodiment of the present invention, similar to the view shown in FIG. 13C.

Other preferred embodiments of the present invention achieve splitting of the sleeve 16 or sleeve portion 18 in different ways. With reference to FIG. 14, for example, an embodiment of the device 10 is there shown in which the splitting mechanism 20 comprises a garrote 66 having a proximal end 68 and a distal end 70. The distal end 70 of the garrote 66 is connected to the interior surface 72 of the sleeve 16, and the garrote 66 extends first between the stent 14 and the sleeve 16, and then proximally of the stent 14. Withdrawal of the proximal end 68 of the garrote 66 splits at least the portion 18 of the sleeve 16 extending over the stent 14. More of the sleeve 16 can be split, if desired, by fixing the distal end 70 of the garrote 66 to the sleeve 16 more proximally of the stent 14.

Figure 16:
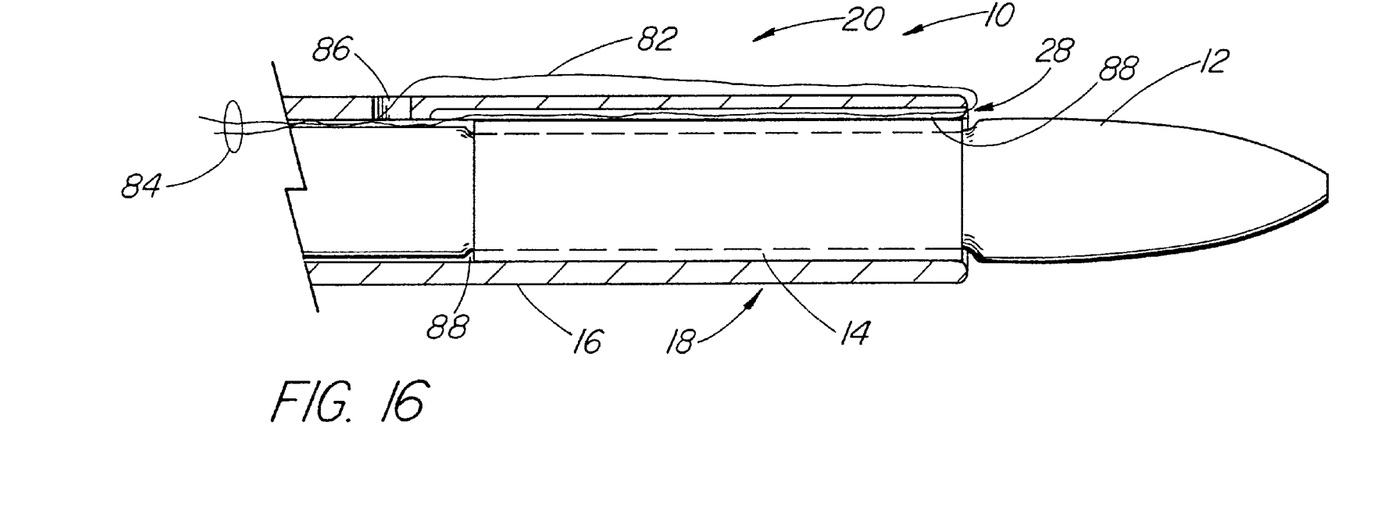
FIG. 16 is a partial sectional side view of still yet another preferred embodiment of the stent deployment device of the present invention.

In still yet another preferred embodiment of the invention depicted in FIG. 16, device 10 comprises a splittable sleeve 16 with sleeve portion 18 extending over stent 14. Proximal sleeve portion 18 includes side port or aperture 86 through which one end 84 of suture 82 is passed from the exterior thereof into passage 88 of the sleeve. This end is first passed through passage 88 and out distal end 28 of the sleeve. The end of the suture 82 is looped back via the exterior of the sheath and back into passage 88 of the sleeve. Either one or both of proximal ends 84 of the suture are pulled with respective to the sleeve to split at least sleeve portion 18. When sleeve portion 18 is split up to side port or aperture 86, the stent 14 self expands or is expanded with a balloon as previously described. Furthermore, suture 82 can be completely withdrawn from the proximal end of sleeve 16.

Figure 15A:
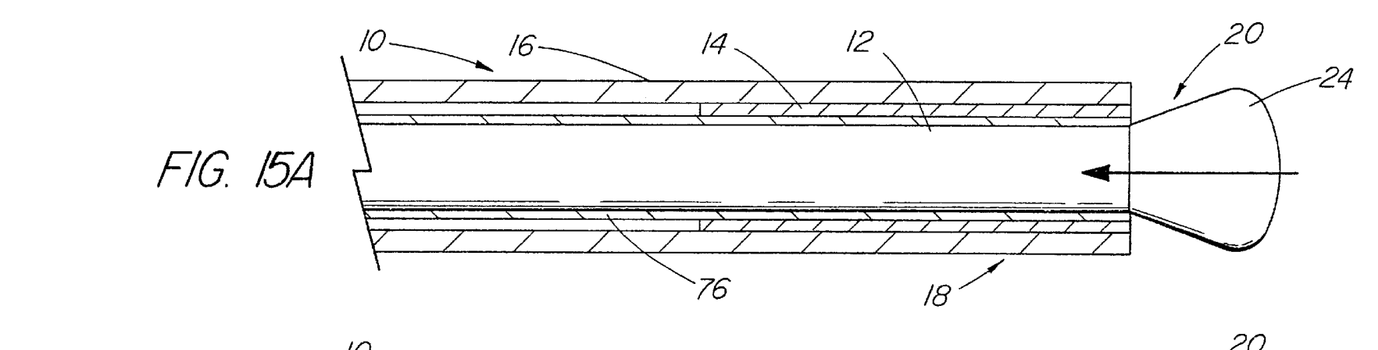
FIGS. 15A through 15C are partial cross-sectional views of additional preferred embodiments of the present invention, similar to the views shown in FIGS. 13C and 14.
Figure 15B:
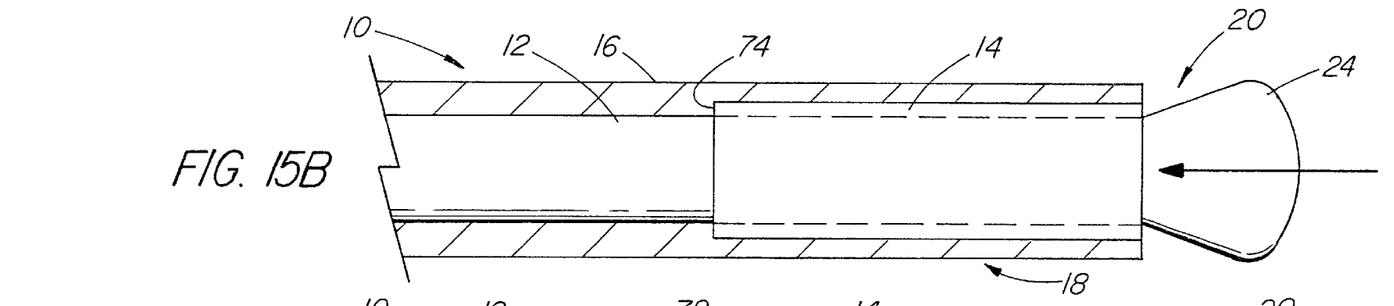
Figure 15C:
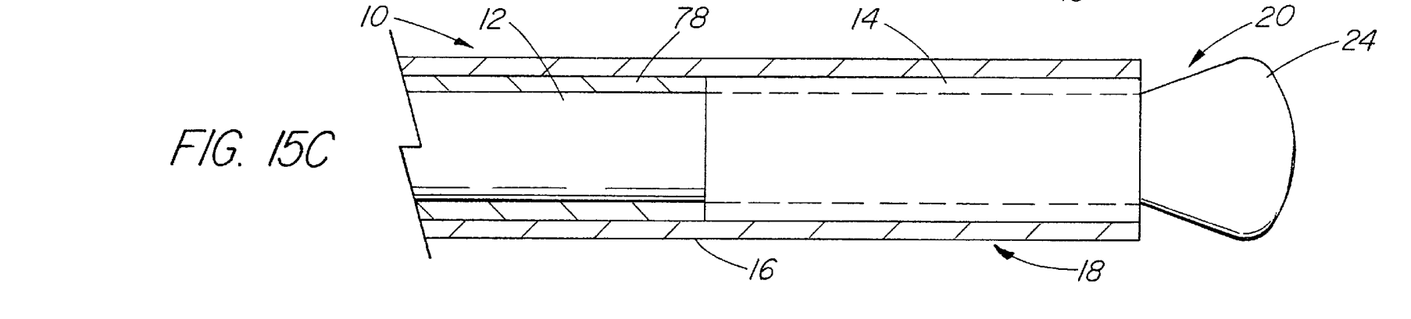

Several further but related embodiments of the stent deployment device 10 of the present invention are shown in FIGS. 15A, 15B and 15C. In each, the mechanism 20 for splitting the sleeve portion 18 is not necessarily a balloon 22, but rather preferably comprises a bulbous end 24 on the catheter 12. The bulbous end 24 is preferably solid, to ensure that splitting of the sleeve 16 or the sleeve portion 18 occurs. However, the bulbous end 24 certainly could be an inflated or inflatable balloon. What is critical is that severing of the bulbous end 24 from the catheter 12 must be avoided.

In any event, these embodiments differ from several of the other described embodiments in that the stent 14 and sleeve portion 18 are not directly positioned over the splitting means 20 (for example, over the balloon 22). Rather, the stent 14 and the sleeve portion 18 are positioned proximally of the bulbous end 24, and it is longitudinal movement of the bulbous end 24 with respect to the sleeve 16 which splits at least the sleeve portion 18 and permits expansion of the stent 14.

These embodiments also differ from one another in the way in which the stent 14 is positioned with respect to the sleeve portion 18. For example, in the embodiment shown in FIG. 15A, the stent 14 is simply received in the open end of the sleeve 16, and a long but relatively thin, lubricious inner sheath 76 is positioned between the stent 14 and the catheter 12, to reduce friction between the sleeve 16 and the catheter 12, and thereby facilitate longitudinal movement of the catheter 12 in the direction of the unlabeled arrow. Alternatively, as shown in FIG. 15B, the inner sheath 76 is omitted, and the stent 14 abutted against a shoulder 74 formed on the interior of the sleeve 16. Finally, as shown in FIG. 15C, the stent 14 is abutted against a relatively shorter, inner sheath or pusher 78, in place of the shoulder 74. The inner sheath or pusher 78 is slidable with respect to the sleeve 16. Which of these specific embodiments is most useful in a given situation is left to the sound discretion of the health care practitioner.

As indicated above, the last several embodiments of the device 10 of the present invention need not include a balloon 22 on the catheter 12.

However, this is not to suggest that a balloon-type catheter 12 and balloon-expandable stent 14 could not be used in those embodiments. To the contrary, it should be clear that the bulbous catheter end 24 could itself be a balloon 22, longitudinally moved in the same way in order to split the sleeve portion 18. Unlike the earlier embodiments incorporating a balloon 22, the stent 14 and sleeve portion 18 are not positioned over the balloon 22, but spaced from it, like the solid bulbous end 24 described above.

Similarly, while it may be preferred to employ self-expanding stents in these embodiments of the present invention, it is certainly possible to employ a stent 14 which is expanded by longitudinal movement of the bulbous catheter end 24 described above.

The methods of using the devices described above should now be evident. The catheter 12 is first introduced to position the stent 14 at the location in a human or veterinary patient at which deployment of the stent 14 is desired. The splitting mechanism 20 is then actuated to split the portion 18 of the sleeve 16 over the stent 14, and expansion and deployment of the stent 14 are permitted to occur. As indicated, the stent can be self-expanding, or can be expanded by the splitting mechanism 20 itself. In either case, the catheter 12 and any desired portion of the sleeve 16 are withdrawn from the patient once the stent 14 is deployed. If the sleeve 16 is fixed to the catheter 12, they are withdrawn together after the deflation of any balloon. If the sleeve 16 is not affixed to the catheter 12, the sleeve 16 can be retracted while any balloon 22 remains inflated, and the catheter 12 withdrawn after deflation of the balloon 22. Any balloon 22 is deflated, of course, by allowing the fluid in the balloon 22 to escape through the catheter 12 and the coupling 32.

The particular elements disclosed in regard to any single one of the embodiments described above may be readily adapted for use in others of the embodiments. For example, the preferentially splittable structure 46 can be employed in any of the disclosed embodiments. The lubricious surface 42 can be positioned in any location as is convenient or desired. Moreover, while all of the disclosed embodiments of the invention employ stents 14 and sleeves 16 which encircle the catheter 12 on which they are carried, the invention contemplates other arrangements for carrying a stent 14 on a catheter 12. The entire sleeve 16 can consist of only the sleeve portion 18 extending over the stent 14. The catheter 12 can, of course, include a lumen for a wire guide, or additional lumens for other purposes. Many other variations on the specific constructions of the catheter 12, the stent 14 and sleeve 16 will be apparent to those skilled in this art, and all of such variations are contemplated within the scope of the present invention.

It should be clear from the foregoing that the present invention provides a stent deployment device which is highly advantageous over prior devices and methods of stent deployment. Initial splitting of the portion of the sleeve over the stent obviates the frictional resistance to withdrawal of the sleeve that would otherwise result from compression of the sleeve upon the stent. The substantial extent of the sleeve portion over the stent provides the device with good uniformity of resistance to kinking during use. Moreover, during use of many of the embodiments of the present invention, the stent is deployed rapidly, because no time is wasted in attempting to remove the sleeve from the patient before expansion of the stent occurs. If a balloon is employed on the catheter, the balloon is advantageously subjected to relatively uniform force during expansion, obviating any risk of damage to the balloon or stent during expansion. The device of the present invention is also advantageous in that its construction is straight-forward and relatively low in cost. Finally, since the device is introduced as a single unit, it is relatively easy to remove in case unexpected patient complications require interruption of the deployment procedure.

Any undisclosed or incidental details of the construction or composition of the various elements of the disclosed embodiment of the present invention are not believed to be critical to the achievement of the advantages of the present invention, so long as the elements possess the characteristics needed for them to perform as disclosed. The selection of these and other details of construction are believed to be well within the ability of one of even rudimentary skills in this area, in view of the present disclosure.

INDUSTRIAL APPLICABILITY

The present invention is useful in performing surgical procedures, and therefore finds applicability in human and veterinary medicine.

It is to be understood, however, that the above-described device is merely an illustrative embodiment of the principles of this invention, and that other devices and methods for using them may be devised by those skilled in the art, without departing from the spirit and scope of the invention. It is also to be understood that the invention is directed to embodiments both comprising and consisting of the disclosed parts.

What is claimed is:

1. A stent deployment device, comprising:
   a catheter;
   a self-expanding stent positioned on the catheter;
   a sleeve carried on the catheter, the sleeve having a portion extending over and containing the stent; and
   a mechanism adjacent to a distal end of sleeve for splitting at least the portion of the sleeve extending over the stent, whereby the mechanism need extend radially outwardly only to an extent required to expand the sleeve for splitting thereof thereby permitting self-expansion of the stent thereafter.

2. The device (10) according to claim 1, wherein the sleeve (16) is composed of polyamide, nylon, polytetrafluoroethylene, polyethylene or a polycaprolactam.

3. The device according to claim 2 further comprising a lubricious outer surface on the sleeve.

4. The device (10) according to claim 3, wherein the lubricious surface (42) comprises a layer (44) of a hydrophilic material.

5. The device (10) according to claim 3, wherein the lubricious surface (42) includes a surface modification of the sleeve (16).

6. The device (10) according to claim 2, wherein at least the portion (18) of the sleeve (16) includes a preferentially splittable, longitudinally extending structure (46).

7. The device (10) according to claim 6, wherein the preferentially splittable structure (46) comprises at least one area (48) of reduced radial thickness.

8. The device (10) according to claim 1, wherein the sleeve (16) includes a proximal end (38) opposite the portion (18) extending over the stent (14), and wherein the mechanism (20) further comprises a means (54) for splitting the sleeve (16) between the proximal end (38) and the portion (18).

9. The device (10) according to claim 1, wherein the sleeve (16) is indistensable.

10. The device according to claim 1, wherein the mechanism comprises an inflatable balloon carried on the catheter and wherein the stent and the portion of the sleeve extending over the stent are positioned over the balloon.

11. A stent deployment device, comprising:
    a catheter;
    a self-expanding stent positioned on the catheter;
    a sleeve carried on the catheter, the sleeve having a portion extending over and containing the stent; and
    a mechanism for splitting at least the portion of the sleeve extending over the stent;
    wherein the mechanism comprises an inflatable balloon carried on the catheter; wherein the stent and the portion of the sleeve extending over the stent are positioned over the balloon; and wherein inflation of the balloon splits at least the portion of the sleeve over the stent, thereby permitting expansion of the stent.

12. The device (10) according to claim 11, wherein the sleeve (16) is composed of polyamide, nylon, polytetrafluoroethylene, polyethylene or a polycaprolactam.

13. The device (10) according to claim 12, wherein at least the portion (18) of the sleeve (16) includes a preferentially splittable, longitudinally extending structure (46).

14. The device (10) according to claim 11, wherein the sleeve (16) includes a proximal end (32) opposite the portion (18) extending over the stent (14), and wherein the mechanism (20) further comprises a means (54) for splitting the sleeve (16) between the proximal end (32) and the portion (18).

15. A stent deployment device, comprising:
    a catheter;
    a self-expanding stent positioned on the catheter;
    a sleeve carried on the catheter, the sleeve having a portion extending over and containing the stent; and
    a mechanism adjacent to a distal end of the sleeve for splitting at least the portion of the sleeve extendin over the stent, thereby permitting expansion of the stent;
    wherein the sleeve is composed of a medical grade, biodegradable material.

16. The device (10) according to claim 15, wherein the biodegradable material is a polyethylene, polypropylene or polyoxypropylene glycolic sugar, or a polylactic sugar.

17. A stent deployment device, comprising:
    a catheter;
    a self-expanding stent positioned on the catheter;
    a sleeve carried on the catheter, the sleeve having a portion extending fully over and containing the stent, wherein at least the portion of the sleeve includes a preferentially splittable, longitudinally extending structure defined by a plurality of longitudinally extending adjacent strips; and
    a mechanism for splitting at least the portion of the sleeve extending over the stent, thereby permitting expansion of the stent;
    wherein the mechanism comprises an inflatable balloon carried on the catheter;
    wherein the stent, and the portion of the sleeve extending over the stent, are positioned over the balloon; and
    wherein expansion of the balloon during inflation splits at least the portion of the sleeve and expands the stent.

18. A stent deployment device, comprising;
    a catheter;
    a self-expanding stent positioned on the catheter;
    a sleeve carried on the catheter, the sleeve being substantially the same length as the catheter and having a proximal end fixed to the catheter, and the sleeve being composed of nylon and having a portion extending fully over and compressing the stent; wherein at least the portion of the sleeve includes a preferentially splittable, longitudinally extending structure comprising at least one area of reduced radial thickness defined by an inward V-shaped notch extending longitudinally therealong; and
    a mechanism for splitting at least the portion of the sleeve extending over the stent, thereby permitting expansion of the stent;

wherein the mechanism comprises an inflatable, nondistending balloon carried on the catheter;

wherein the stent, and the portion of the sleeve extending over the stent, are positioned over the balloon; and wherein expansion of the balloon during inflation splits at least the portion of the sleeve and expands the stent.

* * * * *